United States Patent
Taylor

Patent Number: 5,554,105
Date of Patent: Sep. 10, 1996

[54] PATELLA STABILIZER

[75] Inventor: Dean A. Taylor, Vancouver, Canada

[73] Assignee: Generation II Orthotics, Inc, Richmond, Canada

[21] Appl. No.: 269,976

[22] Filed: Jul. 1, 1994

[51] Int. Cl.$^6$ ........................................... A61F 5/00
[52] U.S. Cl. .................. 602/26; 602/62; 2/24; 128/882
[58] Field of Search ........................ 602/5, 13, 16, 602/23, 26, 60, 63, 62; 2/24; 128/882

[56] References Cited

U.S. PATENT DOCUMENTS

| | | | |
|---|---|---|---|
| 1,622,211 | 3/1927 | Sheehan | 602/26 X |
| 1,666,846 | 4/1928 | Cooper . | |
| 3,902,482 | 9/1975 | Taylor . | |
| 4,024,584 | 5/1977 | Smith . | |
| 4,084,584 | 9/1978 | Detty | 602/26 |
| 4,116,236 | 9/1978 | Albert | 602/26 |
| 4,287,885 | 9/1981 | Applegate . | |
| 4,296,744 | 10/1981 | Palumbo . | |
| 4,466,428 | 8/1984 | McCoy . | |
| 4,490,855 | 1/1985 | Figgie, III et al. . | |
| 4,854,308 | 8/1989 | Drillio | 602/26 X |
| 4,872,448 | 10/1989 | Johnson, Jr. | 602/26 |
| 5,230,697 | 7/1993 | Castillo et al. . | |
| 5,302,169 | 4/1994 | Taylor . | |

FOREIGN PATENT DOCUMENTS 2136294  9/1984  United Kingdom ............. 602/26

OTHER PUBLICATIONS

Exhibit A, Donjoy Products Catalog–Rev A, p. 48.

*Primary Examiner*—Richard J. Apley
*Assistant Examiner*—Kim M. Lee
*Attorney, Agent, or Firm*—Townsend and Townsend and Crew, LLP

[57] ABSTRACT

A patella stabilizer. The stabilizer has a sleeve to be received around a knee of a wearer. There is a support in the sleeve that has a first member to extend from beneath the wear's patella to a point over the wearer's tibia. Second, bifurcated members extend from the first member along each side of the patella when the patella stabilizer is in position on the wearer. In a preferred embodiment, there is a strap that extends around the wearer's leg, over the first member of the stabilizer.

8 Claims, 1 Drawing Sheet

PATELLA STABILIZER

FIELD OF THE INVENTION

This invention relates to a patella stabilizer.

DESCRIPTION OF THE PRIOR ART

The patella, or knee cap, is fixed in its position over the knee by the patella tendon which extends down from the bottom of the patella to the tibia or shin bone. There can be a number of problems with the patella. Simple pain can result from patella hypermobility and patella femoral arthritis (chondramalacia) but relatively complex problems such as a laterally subluxing patella caused by musculature imbalance and/or tibial femoral rotation can occur.

Patella pain can also result from problems relating to the bones, their condition and relation to one another, and to inadequate musculature or imbalance. Patella pain is often caused by over use and irritation of the soft tissue beneath the patella.

The prior art has attempted to provide devices to cure these problems. In general these devices comprise members that are received on each side of the patella, that is a generally U-shaped body attached by a strap or the like. These devices have not been particularly successful.

Prior art known to applicants includes U.S. Pat. No. 5,230,697 to Castillo; U.S. Pat. No. 4,287,885 to Applegate; U.S. Pat. No. 4,296,744 to Palumbo; U.S. Pat. No. 4,466,428 to McCoy; U.S. Pat. No. 4,490,855 to Figgie; U.S. Pat. No. 1,666,846 to Cooper and U.S. Pat. No. 4,024,584 to Smith.

Of the above Castillo disclosed a knee brace comprising an upper frame member and a lower frame member joined at a hinge. The frame member is formed from a fiber reinforced composite material having sufficient rigidity to withstand impact forces yet sufficiently light in weight so as not to impair movement of the knee. The brace is positioned on the leg by means of encircling straps. The brace of Castillo is not specifically designed to stabilize the patella but a patella cup is shown and is used to protect the knee.

Applegate disclose a knee brace that includes an elastic sleeve having an opening to be positioned about the patella. Annular pads can be removably positioned about the knee to stabilize the patella.

Palumbo disclose a patella brace that is a combination of a sleeve having an opening, a strap and a bracing pad system to stabilize the patella.

McCoy disclose a patella support apparatus that includes a strap and an annular brace member having pads.

Figgie discloses a further example of a knee pad including an upper pad, a lower pad and a cover. A single strap is used to attach the device to a wearer. The pad is not specifically designed to stabilize the patella. Cooper shows a knee pad that includes cross straps to locate the pad securely about the knee of the wearer and Smith discloses a protective garment that includes a knee pad that is held in place over the knee by a sock worn by the wearer.

SUMMARY OF THE INVENTION

The present invention seeks to cure the deficiencies of the prior art. In experiments conducted the patella stabilizer of the invention has provided excellent results in stabilizing the patella.

Accordingly, the present invention provides a patella stabilizer comprising a sleeve to be received around a knee of a wearer; a support in the sleeve comprising a first member to extend from beneath the wearer's patella to a point over the wearer's tibia; and a second, bifurcated member to extend from the first member along each side of the patella when the patella stabilizer is in position on the wearer.

In a preferred embodiment the stabilizer includes a strap to extend around the wearer's leg, over the first member of the stabilizer.

DESCRIPTION OF THE PREFERRED EMBODIMENTS

Figure 1:
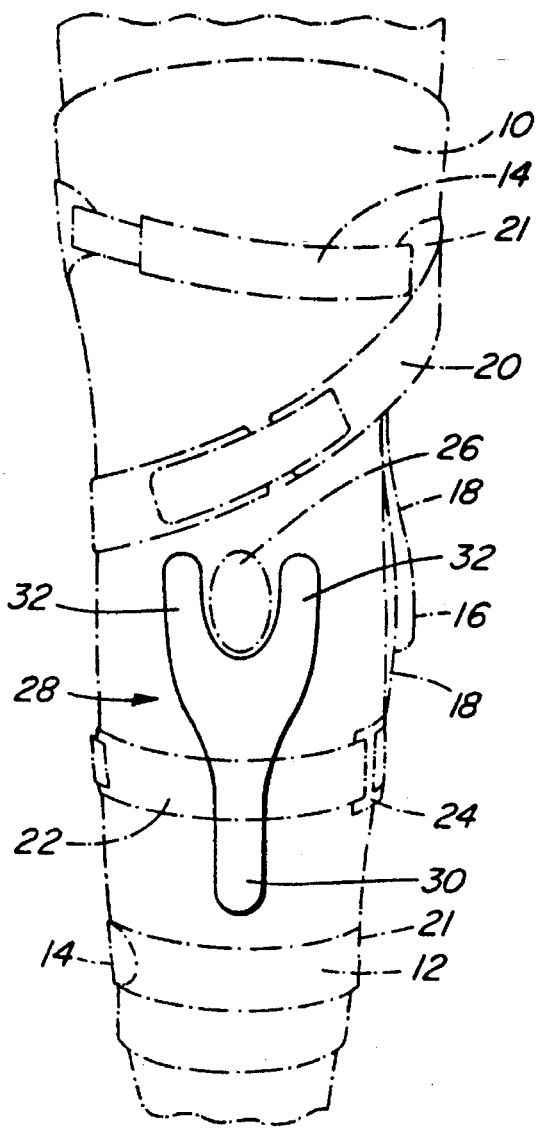
FIG. 1 shows a stabilizer according to the present invention.

FIG. 1 shows a patella stabilizer comprising a sleeve 10, typically of neoprene, to be received around the knee of a wearer of the stabilizer.

The main structure of the sleeve 10 is known from the prior art.

The brace comprises built-in, relatively rigid ribs 12 of approximately semi-circular shape at the top and bottom. Only the bottom rib 12 is shown. The upper rib extends behind the leg. The ends of the semi-circular ribs 12 are attached by straps 14. The stabilizer also includes a hinge 16 and members 18 extending from it. Such hinges are well known in the art, for example, from commonly owned U.S. Pat. No. 5,302,169 issued 12 Apr. 1994 and U.S. Pat. No. 3,902,482 issued 2 Sep. 1975, the disclosures of which references are incorporated herein by reference.

The embodiment of FIG. 1 also shows a strap 20 that extends around the wearer's leg, from anchor points 21 on the ribs 12. In the preferred embodiment illustrated in FIG. 1 there is a strap 22 that extends around the wearer's leg.

Typically these straps 14, 20 and 22 are engaged in eyelets 24 (only one of which is shown) and are provided with hook and eye fasteners, for example available under the Trademark Velcro; to secure them in position.

The sleeve 10 includes an opening 26, generally fitting over the knee cap and assisting in location of the sleeve 10 on the knee. The patella stabilizer includes a support 28 comprising a first member 30, to extend from beneath the wearer's patella, as shown particularly in FIG. 1, to a point over the wearer's tibia. Second, bifurcated members 32 extend from the first member 30 along each side of the patella. Strap 22 of the preferred embodiment lies over the first member 30 when the stabilizer is in its useful position on a patient.

The support 28 is preferably separate from the sleeve 10 and is attachable to the sleeve to fix it in position relative to the sleeve. Hook and eye fasteners again may be used on the sleeve and on the stabilizer.

The support 28 is typically flexible, for example of closed cell plastic foam or a felt.

Figure 2:
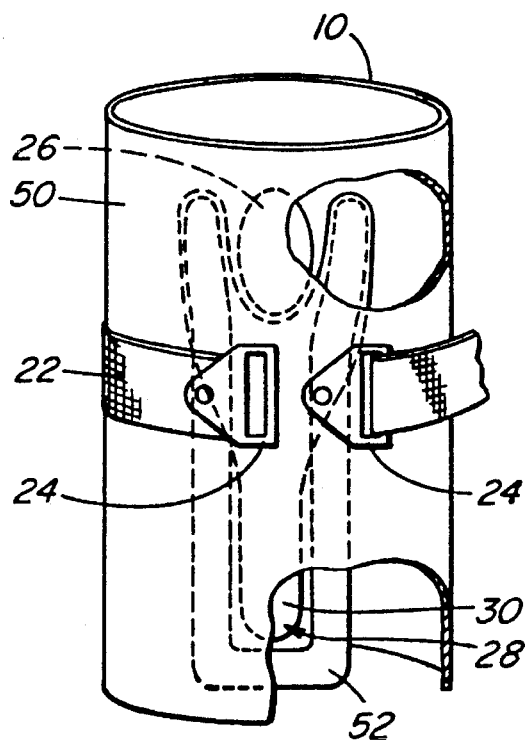
FIG. 2 shows a second embodiment of a stabilizer according to the invention.

The embodiment of FIG. 2 is a simplified version of FIG. 1. It comprises a simple elastic fabric sleeve 50 having a U-shaped stiffener 52 in it. The stiffener 52 is relatively rigid but not so rigid as to prevent the stabilizer conforming to the leg of the wearer. It may, for example, be of a polyamide. The stiffener 52 may be sewn into sleeve 50. Again there is an opening 32, to be located over the knee cap, and support 28 is attached as in the main embodiment of FIG. 1. Strap 22 is again provided. It extends through an eyelet 24, back on itself and is located, when in use, by a hook and eye fastener.

The first member 30 of the support 28 is of prime importance. It is also markedly preferable that the member 30 be supported by the strap 22.

The device of the invention is effective in cradling the patella, thus resisting lateral shifting. The support acts as a buttress. The patella tendon, which extends down from the bottom of the patella to the tibia, is tightened by the pressure on the member 30 of the support.

In the embodiment of FIG. 1 the cross strap 20 is believed to assist in stabilizing the patella by helping to locate the stabilizer about the patella. The support 28 abuts the strap 20 so that support 28 cannot move away from the knee cap. As the support is attached to the stabilizer, the whole device is kept properly located.

In successful experimental work conducted so far the support 28 has a thickness of about ⅜ to ½ inches. It is not believed this thickness is critical but it has provided an adequate compromise of effectiveness and comfort.

The length of the member 30 must be sufficient to enable it to extend to the end of the patella tendon and slightly beyond. It seems to be of importance that in addition to stabilizing the patella by supporting the sides of the patella, the tendon is also supported and stressed.

In addition to the foam plastic and felt the support 28 may simply comprise inflatable air pockets sewn inside the sleeve and having the same effect. A simple pump can be used to inflate these pockets through a valve.

The present invention is believed to be effective because it can be consistently positioned on the leg and because it exerts pressure on the patella tendon. Strap 22 is of value in this regard. In the case of the embodiment of FIG. 2, the stabilizer is further stiffened laterally by the stiffener 52 sewn to the sleeve between the support 28 and the sleeve 50.

In both FIGS. 1 and 2, the sleeve 10 holds the support 28 to the patient's leg throughout the full range of movement of the knee. The sleeve 10 tends to do more from a functional standpoint when the knee flexes. The sleeve 10 keeps the support 28 engaged with the patella, forcing it to move with the leg.

It is also believed that lateral patella subluxation can take place in some instances by relative rotation of the tibia and the femur. In these circumstances the patella tendon tends to move with the external rotation of the tibia, pulling the patella. The embodiment of FIG. 1 is particularly effective in these circumstances although it is also effective for stabilizing the patella in all circumstances.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

I claim:

1. A patella stabilizer comprising:

a sleeve adapted to be received around a knee of a wearer;

a generally Y-shaped first support in the sleeve comprising a first member and a pair of second members, said first member being adapted to extend beneath the wearer's patella to a point over the wearer's tibia;

said second members being bifurcated members structured and arranged to extend from the first member along each side of the wearer's patella when the patella stabilizer is in position on the wearer;

a relatively rigid second support having a generally U-shaped opening with sides, the rigid second support being located inside the sleeve with the sides of the opening extending upwardly, beneath and alongside the wearer's patella and said first member when the stabilizer is in use whereby the first support and the rigid second support together cradle the patella in order to prevent lateral shifting; and a strap configured to extend around the wearer's leg over the first and second members.

2. A stabilizer as claimed in claim 1 in which the first support is separate from the sleeve.

3. A stabilizer as claimed in claim 2 in which the first support is attachable to the sleeve to fix a position relative to the sleeve.

4. A stabilizer as claimed in claim 3 in which the first support is attached to the sleeve by hook and eye fasteners formed on said sleeve and said support.

5. A stabilizer as claimed in claim 1 in which the first support is flexible.

6. A stabilizer as claimed in claim 5 in which the first support comprises an inflatable air pocket.

7. A stabilizer as claimed in claim 5 in which the first support is a felt.

8. A stabilizer as claimed in claim 5 in which the first support is a foamed plastic.

* * * * *